United States Patent [19]
Erskine et al.

[11] Patent Number: 5,848,997
[45] Date of Patent: Dec. 15, 1998

[54] DISCONNECT FOR MEDICAL ACCESS DEVICES

[75] Inventors: Timothy J. Erskine; Glade Howell, both of Sandy, Utah

[73] Assignee: Becton Dickinson and Company, Franklin Lakes, N.J.

[21] Appl. No.: 615,563

[22] Filed: Mar. 15, 1996

[51] Int. Cl.$^6$ .................................................. A61M 25/00
[52] U.S. Cl. .......................... 604/283; 604/905; 604/256
[58] Field of Search .................................. 604/283, 256, 604/905; 137/15, 614.05

[56] References Cited

U.S. PATENT DOCUMENTS

| | | | |
|---|---|---|---|
| 5,108,380 | 4/1992 | Herlitze et al. | 604/283 |
| 5,269,771 | 12/1993 | Thomas et al. | 604/213 |
| 5,322,518 | 6/1994 | Schneider et al. | 604/247 |
| 5,393,101 | 2/1995 | Matkovich | 285/3 |
| 5,492,147 | 2/1996 | Challender et al. | 604/256 |

OTHER PUBLICATIONS

"Rare Complications of Vascular Access Devices," by Rebecca J. Ingle, Seminars in Oncology Nursing, vol. 11, No. 3 (Aug.) 1995, pp. 184–193.

"Percutaneous central iv access in the neonate: experience with 535 silastic catheters," by A–P Neubauer, Acta Paediatr 84, pp. 756–760, 1995.

"Central venous catheters in the emergency department: Access, utilization, and problem solving," by Bradley J. Dyer, M.D., et al., Pediatric Emergency Care, vol. 11, No. 2, pp. 112–117.

"230 Patient Years of Experience With Home Long–Term Parenteral Nutrition in Childhood: Natural History and Life of Central Venous Catheters," by A.A. Moukarzel, et al., Journal of Pediatric Surgery, vol. 29, No. 10 (Oct.), 1994, pp. 1323–1327.

"Infectious Morbidity Associatged with Long–Term Use of Venous Access Devices in Patients with Cancer," by Jeffrey S. Groeger, M.D., et al., Annals of Internal Medicine, vol. 119, No. 12, Dec. 15, 1993, pp. 1168–1174.

"Central Venous Catheter With Subcutaneous Injection Port (Port–A–Cath): 8 Years Clinical Follow Up With Children," by F. Wesenberg, M.D., et al., Pediatric Hematology and Oncology 1993, vol. 10, pp. 233–239.

"Breakage of an Embolized Intravascular Catheter Fragment: A Complication of Nonsurgical Transvenous Retrieval," by Terry D. Bauch, M.D., et al., Journal of Parenteral And Enteral Nurtition, vol. 16, No. 2, pp. 175–177.

"Extradural vein puncture—an avoidable complication," by B.J. Hendley, Anaesthesia, Dec.1991, 46(12): 1092.

(List continued on next page.)

Primary Examiner—John D. Yasko
Attorney, Agent, or Firm—Eric M. Lee

[57] ABSTRACT

A disconnect device for placement in a medical tubing set of the present invention includes a first portion with a first passageway therethrough that has a first valve therein. While the first valve is biased in a normally closed position to close the first passageway, it is operative to an open position. The disconnect device of the invention has a second portion with a second passageway therethrough that has a second valve therein. The second valve is also biased in a normally closed position to close the second passageway and it also is operative to an open position. The second portion is releasably attached to the first portion, connecting the first and second passageways in fluid communication, to overcome the bias of the first valve and the second valve, to open the valves and to allow a fluid flow through the device. When a preselected force, that is, for example, less than a force necessary to physically disrupt a medical access device attached to the tubing set, is applied to the second portion, it is detached from the first portion. With this detachment, the first valve and the second valve are operative to their normally closed positions substantially to stop fluid flow from the fluid reservoir and the medical access device.

12 Claims, 16 Drawing Sheets

OTHER PUBLICATIONS

"Impact on Patient Care, 2652 PIC Catheter Days in the Alternative Setting," by Susan Markel, BSN, CNSN, CRNI, et al., Journal of Intravenous Nursing, vol. 13, No. 6, pp. 347–351.

"Central Venous Catheter Stiffness and its Relation to Vascular Perforation," by A.D. Berstein, et al., Anaesthesia and Intensive Care, vol. 16, No. 3, Aug. 1988, pp. 342–351.

Impact on Patient Care, 2652 PIC Catheter Days in the Alternative Setting, Markel and Reynen, J. Intraven. Nurs. 13(6), 1990; pp. 347–351.

Breakage of an Embolized Intravascular Catheter Fragment: A Complication of Nonsurgical Transvenous Retrieval, Bauch et al, J. Paren. and Ent. Nutr. 16(2), 1993; pp. 175–177.

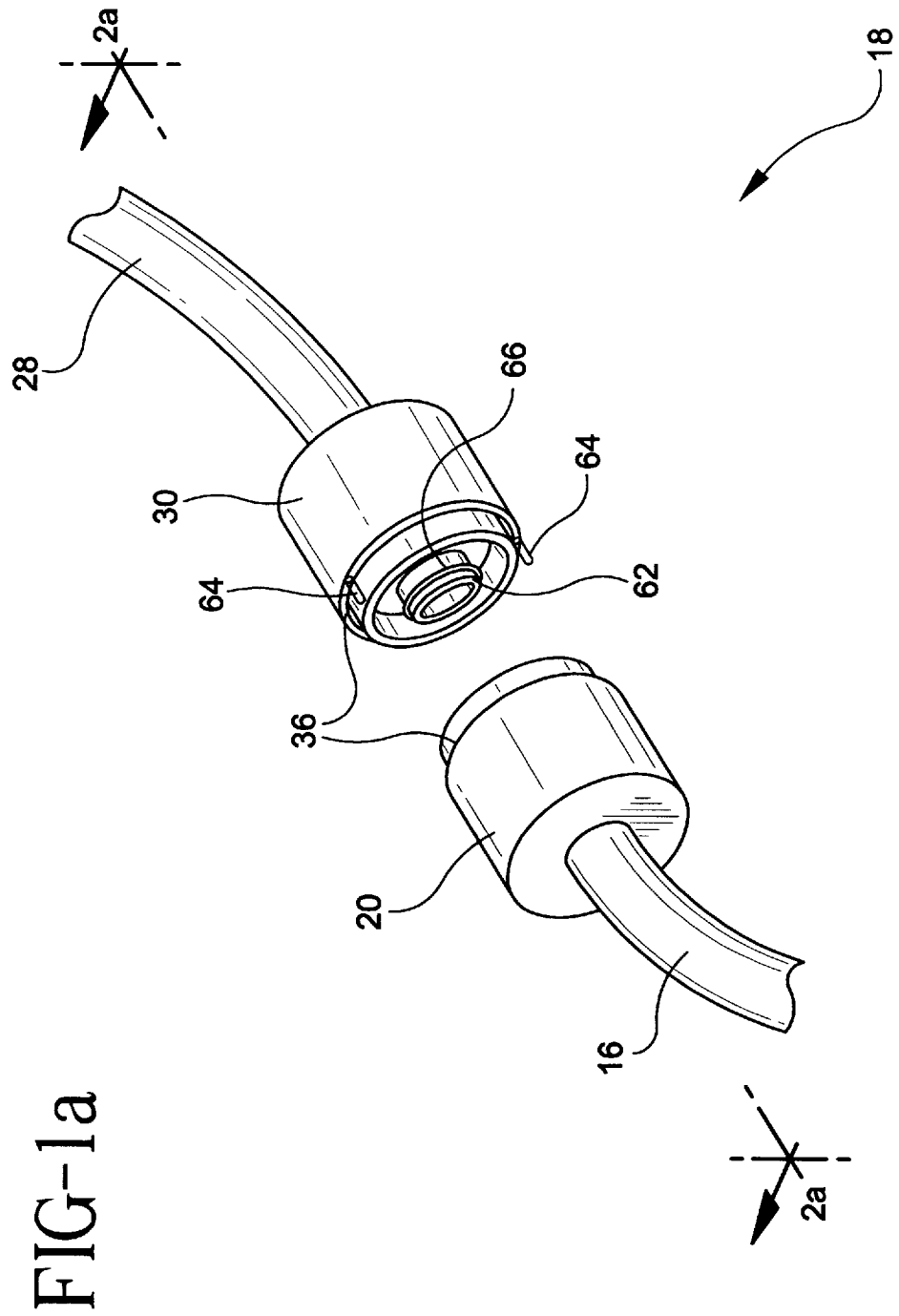

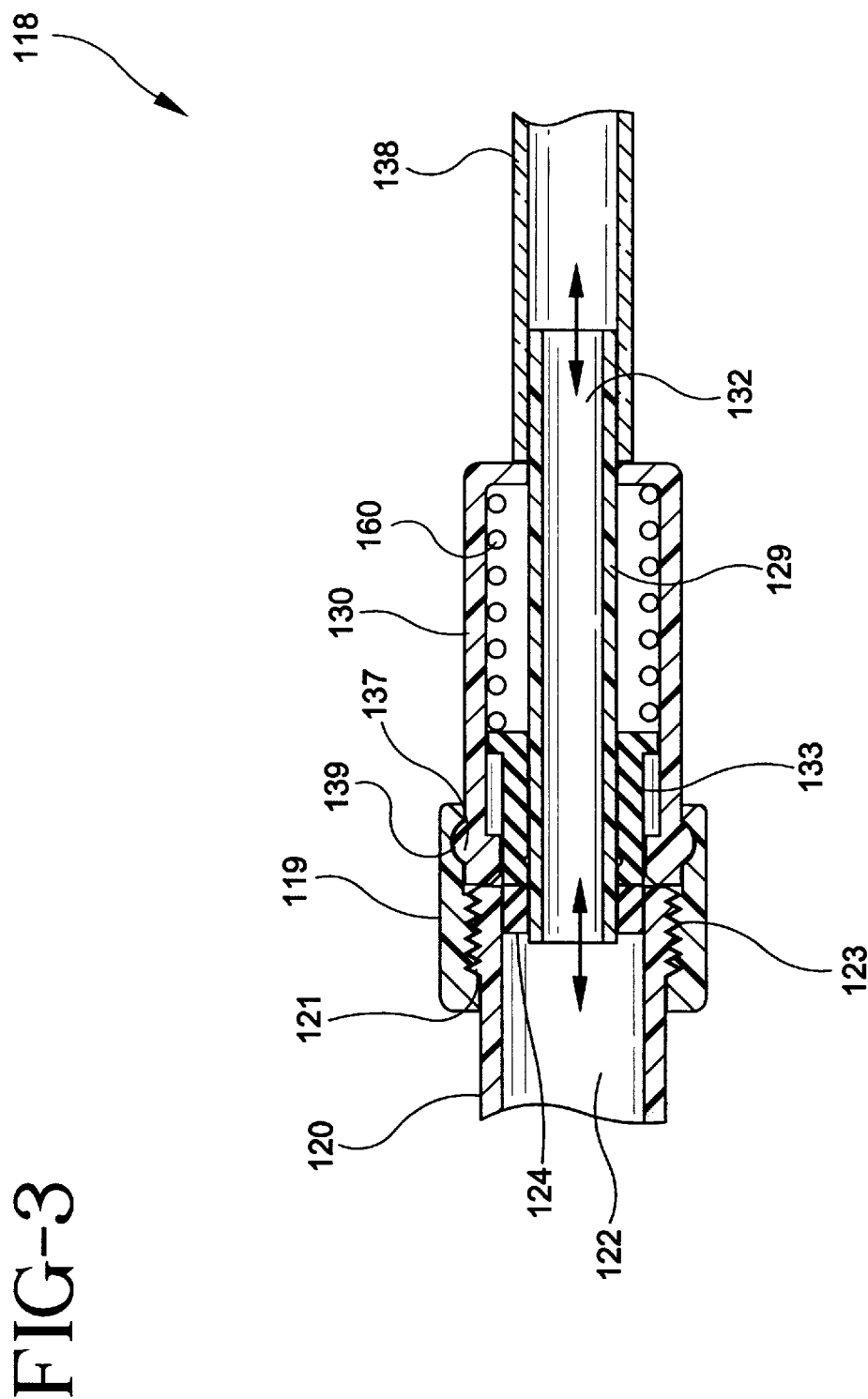

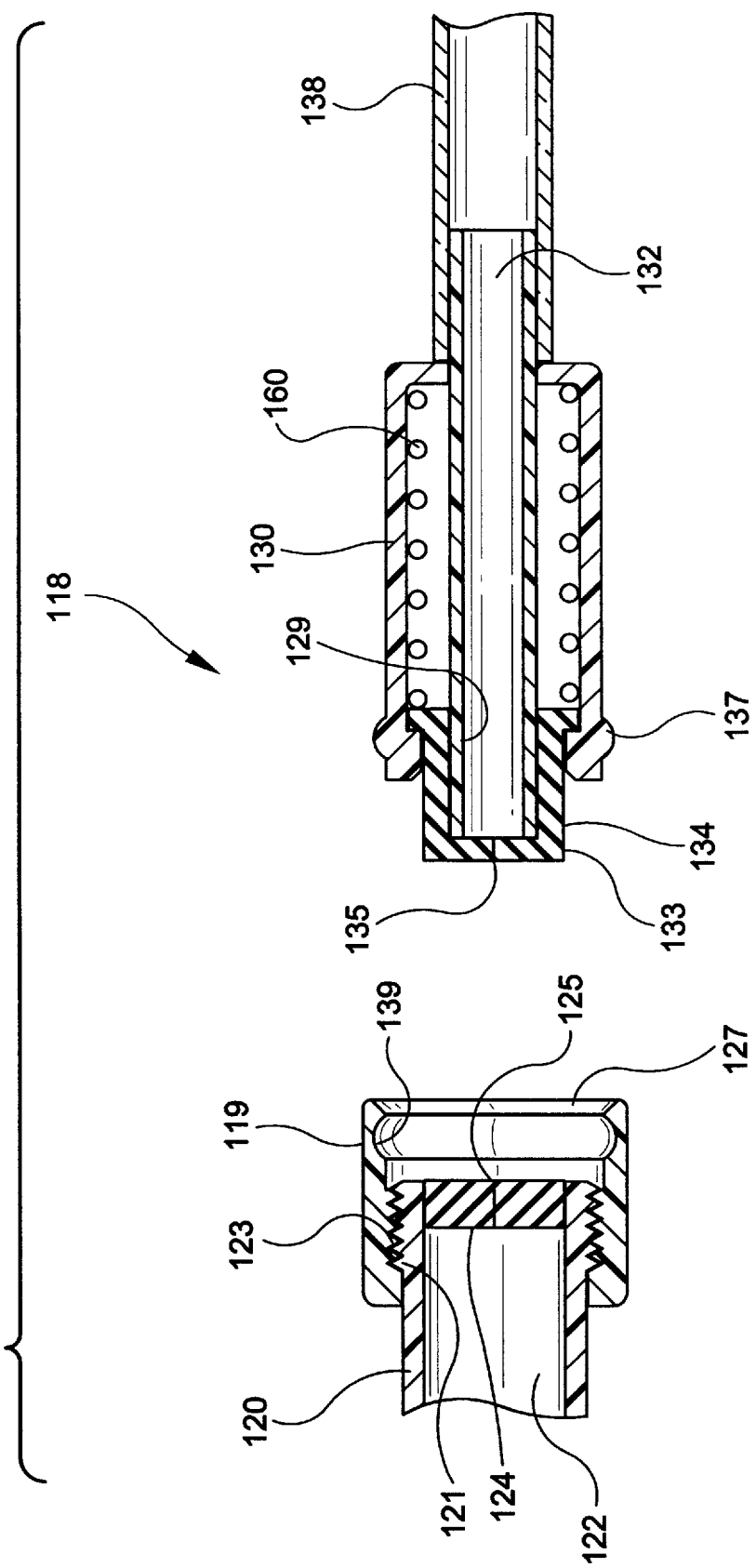

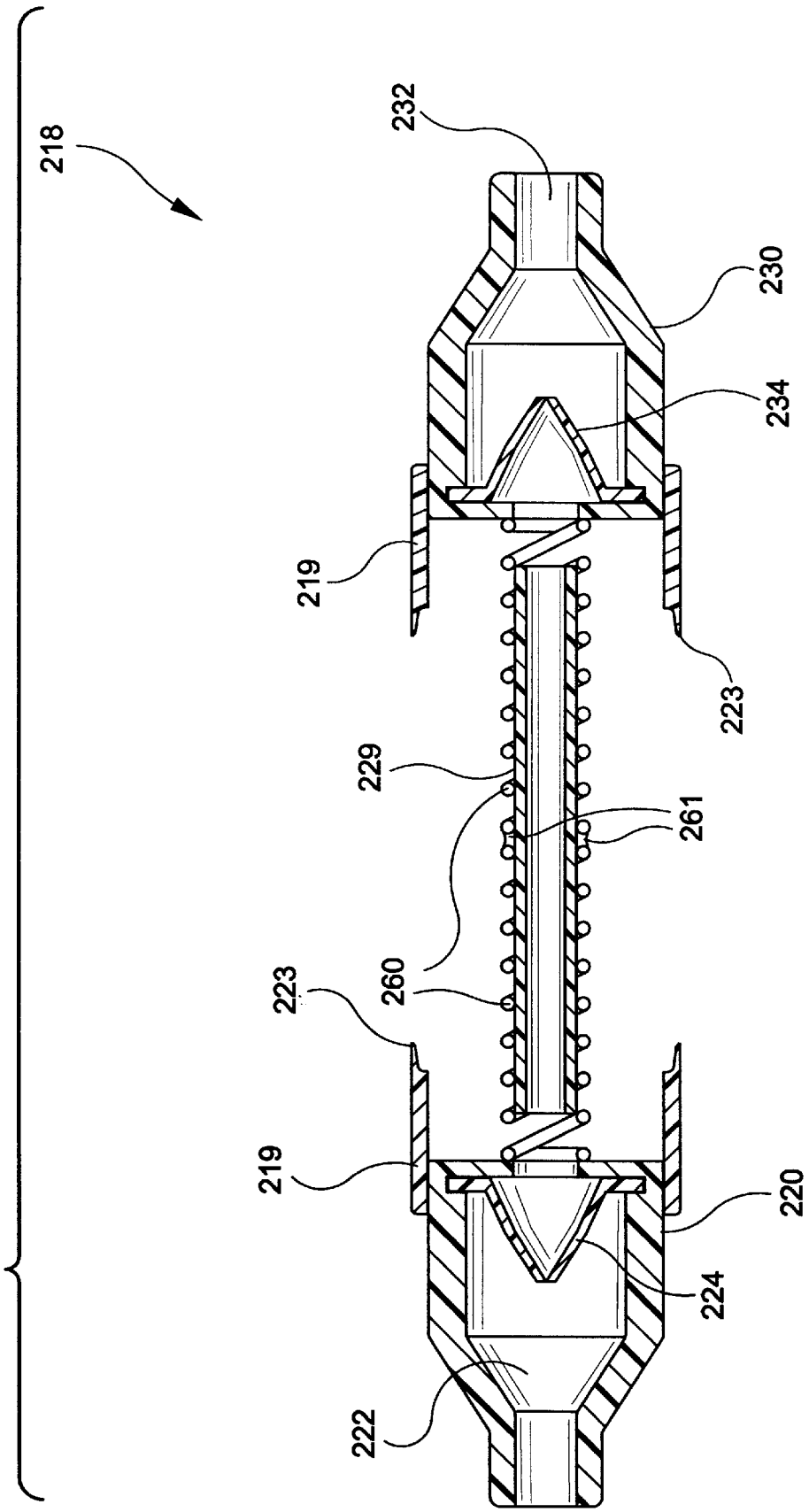

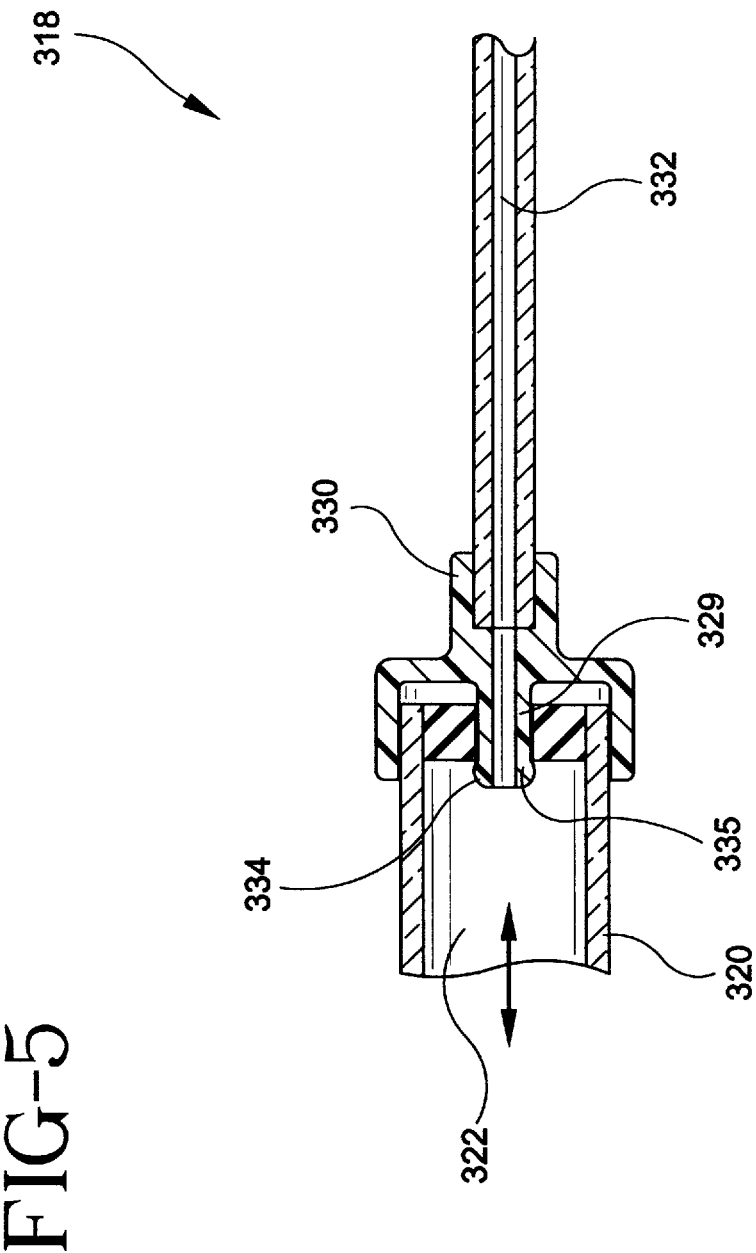

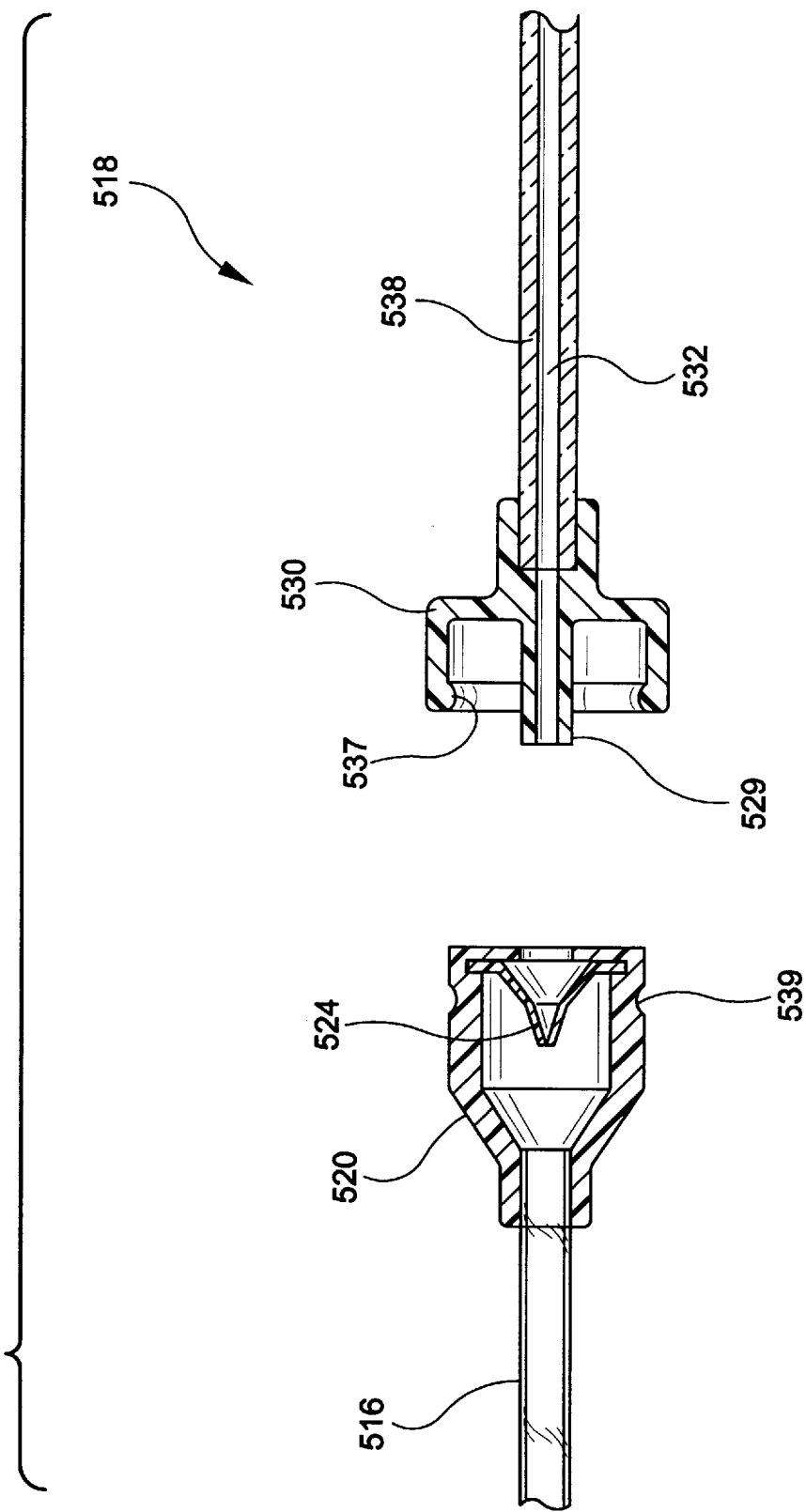

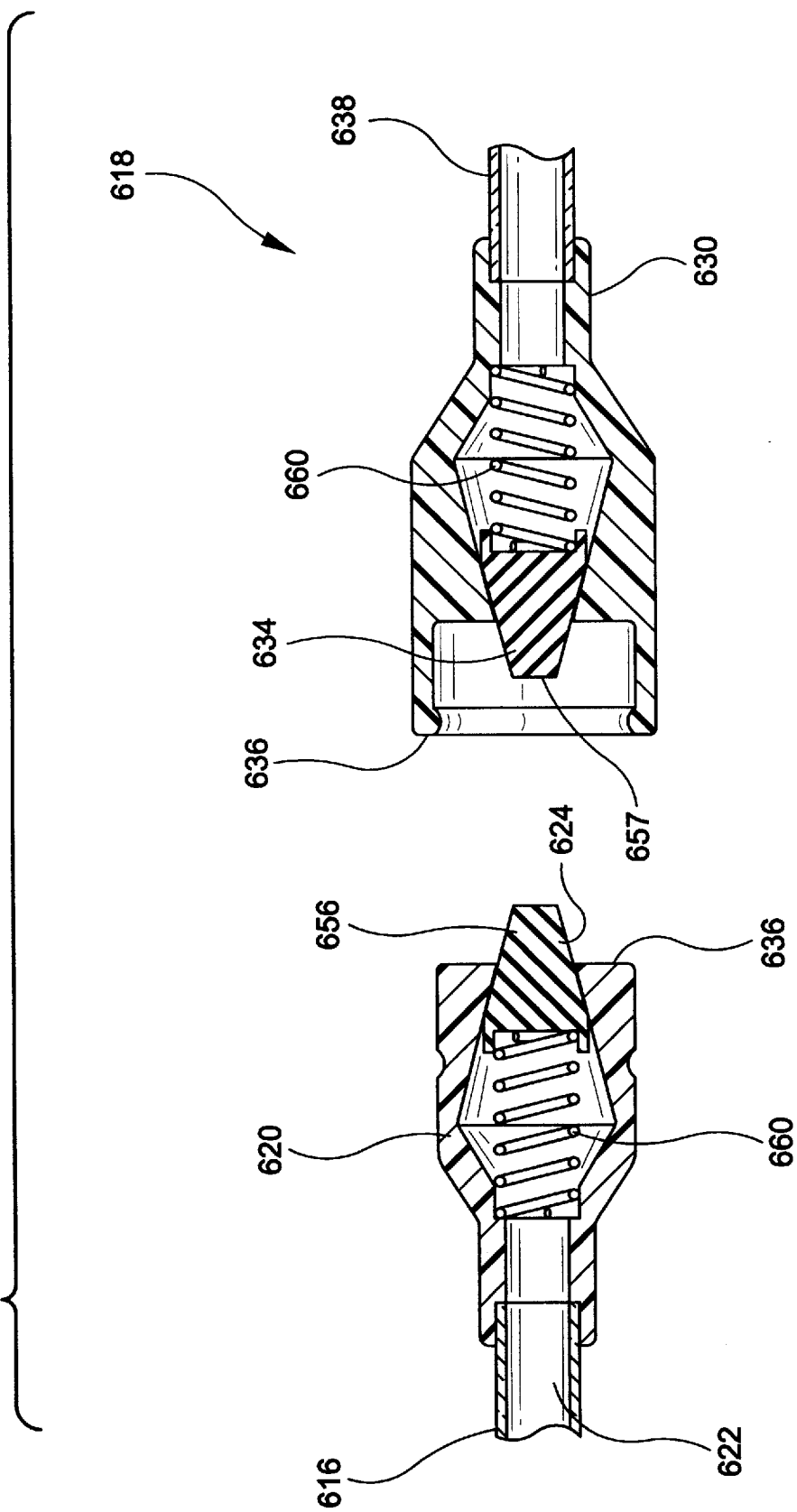

DISCONNECT FOR MEDICAL ACCESS DEVICES

FIELD OF INVENTION

The present invention is related to medical access devices, and more particularly to a disconnect device for medical tubing.

BACKGROUND

Medical access devices such as intravenous catheters, feeding tubes for total parental nutrition (TPN) and the like have long been used in treatment of hospitalized patients. Historically, the actual penetration device was a rigid metal needle and the usage was almost exclusively on patients who were substantially confined to bed. The confinement to bed or at least the immobilization of a limb where the catheter was placed was necessitated because nearly any movement of the rigid metal needle would cause some trauma to the blood vessel or organ where the device was placed.

The development of biocompatible polymeric materials led to the development of many types of flexible medical access devices such as peripheral intravenous catheters, central intravenous catheters, feeding tubes, drains and the like formed from the flexible materials. Since these devices are flexible, a degree of movement of the body around the catheter generally does not result in significant trauma to the organ or blood vessel like that caused by movement of rigid steel needle devices. As medical practitioners became more comfortable with the flexible medical access devices, they began to allow patients with catheters more freedom of movement. Additionally, since the newer flexible devices caused less trauma, practitioners began to leave the devices in place for longer and longer periods. Devices are now available that are usable for fully ambulatory patients that are living at home and not hospitalized. As a result, patients with medical access devices are exposed to many more opportunities to cause physical damage to their devices. Additionally, pediatric, uncooperative or disturbed patients may also disrupt a fluid delivery set and cause physical damage to their medical access device.

There are reports in the literature of physical damage to peripheral intravenous catheters caused by active patients inadvertently catching the fluid line on an object or confused patients damaging their catheter. These reports include physical disruption of medical access devices by a tripping accident, an ill-advised movement or as a result of an confused patient's thrashing about. Commonly used medical tubing sets incorporate polyvinylchloride (PVC) tubing to connect fluid reservoirs and infusion pumps to medical access devices, i.e., catheters and the like. This PVC tubing commonly has a break-force of about ten kilograms or more. A force of about three kilograms removes the tape from the skin when a common taping technique for securing a catheter is used. Catheters also often are secured to the skin with sutures. At the least, a force applied to the sutures would cause significant discomfort to the patient. When an accidental force is applied to the PVC tubing set, the tubing generally does not break, instead it often transfers the force to the medical access device. The force possibly pulls the device off or out of the patient, or worse yet, breaks it off, possibly leaving a portion of the device inside the patient. The soft silicone rubber tubing, in sizes commonly used in catheters for long term implantation, has a break force of less than about one kilogram. Representative of reports in the medical literature regarding difficulties with long-term catheter placement is a paper by Markel and Reynen in the J. Intraven. Nurs. 13(6), 1990; pp347–351, that reports a study of catheter usage experience. Bauch et al. in the J. Paren. and Ent. Nutr. 15(2), 1993; pp175–177, report on the difficulties of retrieval of a portion of a broken-off catheter.

Since the usage of long-term implantation catheters in fully ambulatory patients is now common, more and more patients are potentially being exposed to situations where they may cause physical damage to their catheters while the catheters are being used for fluid infusion. Thus, a disconnect device that detaches the tubing set from the patient when a force is applied to the tubing that potentially could physically disrupt the implanted device would provide a benefit to the field of infusion therapy. Such a disconnect device is described below.

SUMMARY

A disconnect device for placement in a medical tubing set of the present invention includes a first portion with a first passageway therethrough that has a first valve therein. While the first valve is biased in a normally closed position to close the first passageway, it is operative to an open position. The disconnect device of the invention has a second portion with a second passageway therethrough that has a second valve therein. The second valve is also biased in a normally closed position to close the second passageway and it also is operative to an open position. The second portion is releasably attached to the first portion, connecting the first and second passageways in fluid communication, to overcome the bias of the first valve and the second valve, to open the valves and to allow a fluid flow through the disconnect. When a preselected force, for example, a force that is less than a force necessary to physically disrupt a medical access device attached to the tubing set, is applied to the disconnect device of the invention, the second portion is detached from the first portion. With this detachment, the first valve and the second valve are operative to their normally closed positions substantially to stop fluid flow from the fluid reservoir and the medical access device.

Commonly used medical tubing sets incorporate polyvinylchloride (PVC) or similar tubing to connect fluid reservoirs and infusion pumps to medical access devices, i.e., catheters and the like. This PVC tubing commonly has a break-force of about ten kilograms or more. When an accidental force is applied to this tubing, the tubing generally does not break, instead it often transfers the force to the medical access device. This may result in possibly pulling the device off or out of the patient, or worse yet, breaking it off, possibly leaving a portion of the device inside the patient. The disconnect device of the invention substantially eliminates these potentially lethal incidents by disconnecting the tubing with an application of force that is less than the force that would potentially physically disrupt the medial access device. The disconnect device of the invention then shuts off the fluid flow from the fluid reservoir, substantially prevents loss of blood from the patient, and substantially eliminates physical disruption of the medical access device.

BRIEF DESCRIPTION OF THE DRAWINGS

FIG. 1a is a perspective view of the disconnect device of the present invention from FIG. 1, as disconnected;

FIG. 2a is a schematic cross-sectional view of the preferred disconnect device of FIG. 1a along the line 2a—2a;

FIG. 3 is a schematic cross-sectional view, analogous to FIG. 2, of an alternative embodiment of the disconnect device of the present invention;

FIG. 3a is a schematic cross-sectional view, analogous to FIG. 2a, of the disconnect device of FIG. 3, as disconnected;

FIG. 4a is a schematic cross-sectional view, analogous to FIG. 2a, of the disconnect device of FIG. 4, as disconnected;

FIG. 5 is a schematic cross-sectional view, analogous to FIG. 2, of yet another embodiment of the present invention;

FIG. 7a is a schematic cross-sectional view, analogous to FIG. 2a, of the disconnect device of FIG. 7, as disconnected;

FIG. 8a is a schematic cross-sectional view, analogous to FIG. 2a, of the disconnect device of FIG. 8, as disconnected.

DETAILED DESCRIPTION

Figure 1:
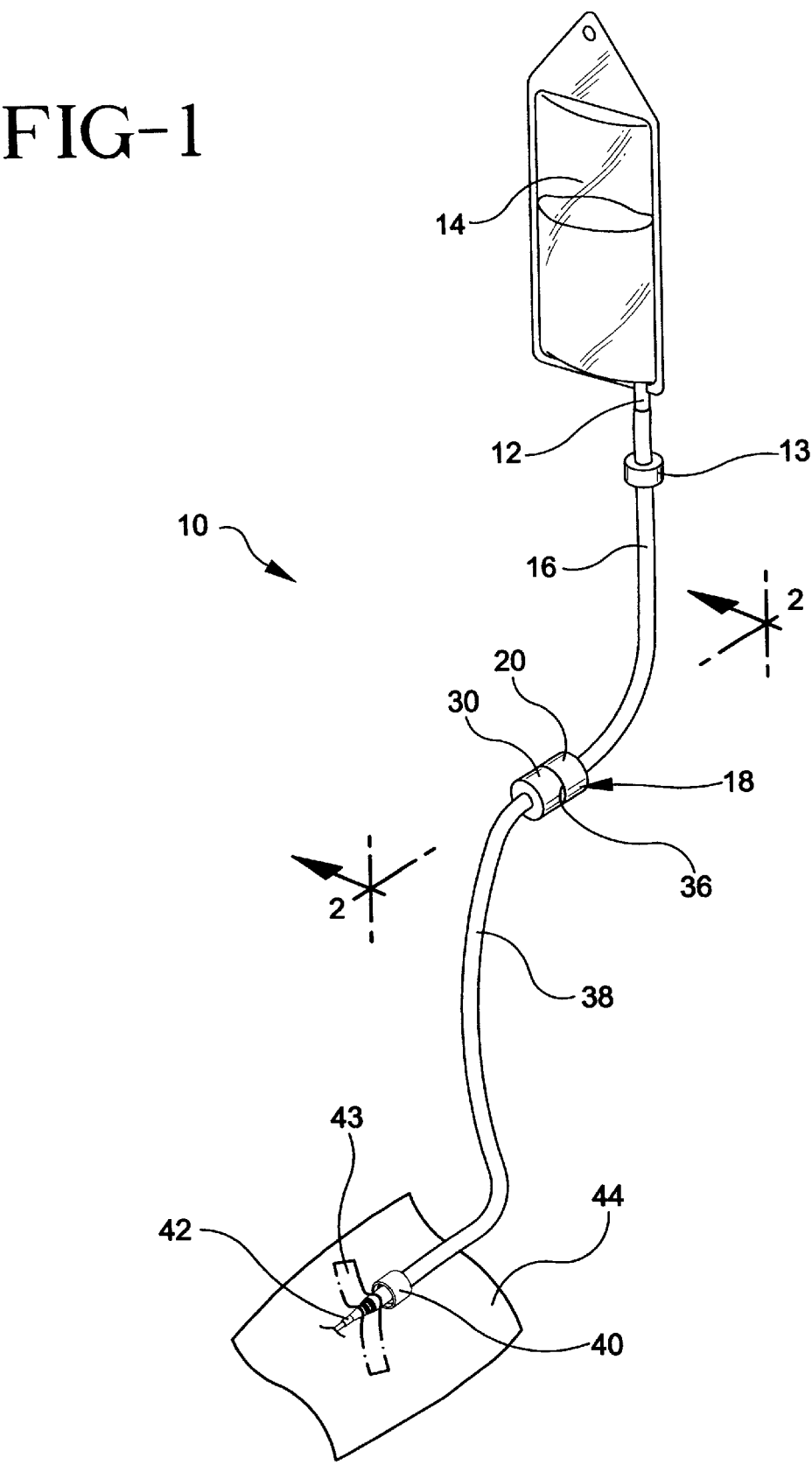
FIG. 1 is a schematic perspective view of a preferred tubing set having a preferred disconnect of the device present invention as used to connect a fluid reservoir to an intravenous catheter in a patient.

While this invention is satisfied by embodiments in many different forms, there are shown in the drawings and herein described in detail preferred embodiments of the invention with the understanding that the present disclosure is to be considered exemplary of the principles of the invention and is not considered to limit the invention to the embodiments illustrated. The scope of the invention is measured by the appended claims and their equivalents. In this description, the term "proximal" refers to the end of the device closest to a fluid reservoir, with the term "distal" referring to the end of the device away from the fluid reservoir.

Figure 2:
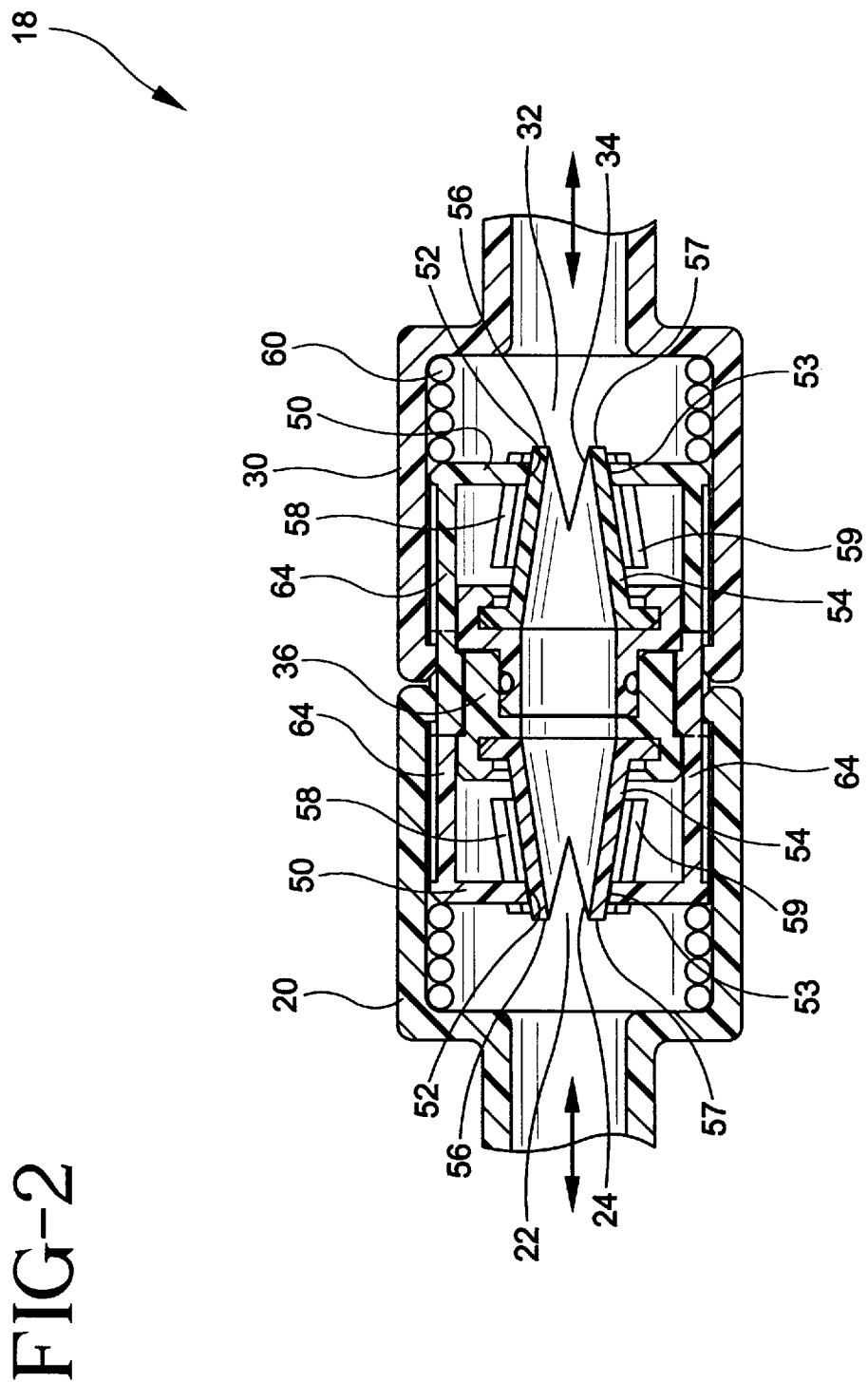
FIG. 2 is a schematic cross-sectional view of the preferred disconnect device of FIG. 1 along the line 2—2.
Figure 2A:
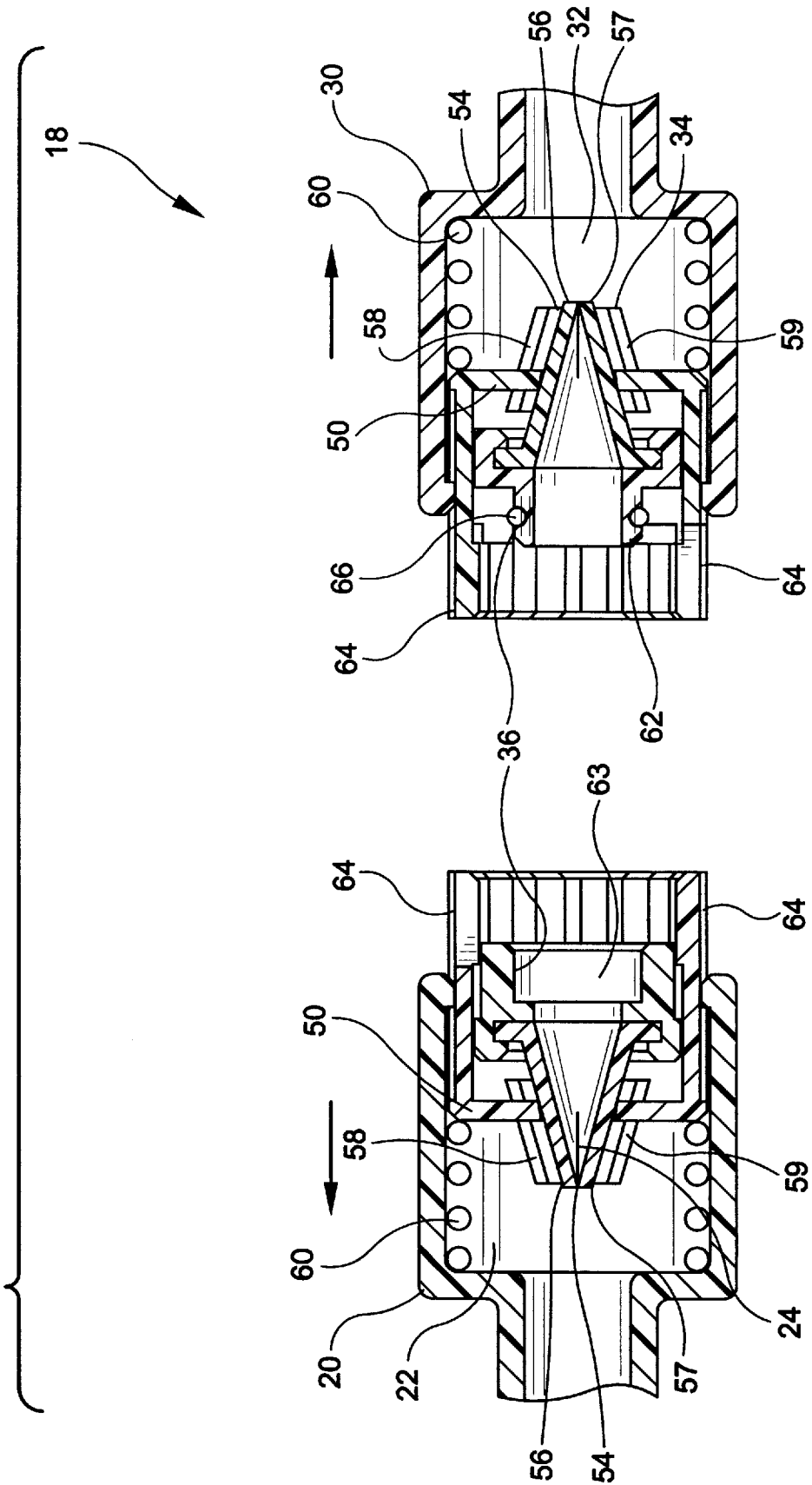

Referring to FIGS. 1, 1a, 2 and 2a, a preferred medical tubing set 10 of the present invention includes a proximal adapter 12 to attach tubing set 10 to a fluid reservoir 14. Preferred tubing set 10 has a proximal tubing 16 in fluid communication to proximal adapter 12. The preferred tubing set may also include a flow indicator 13. Proximal adapter 12 may also include a blunt cannula or other connection device suitable for connection to commonly available fluid reservoirs. Set 10 has a disconnect device 18 having a first portion 20 attached to proximal tubing 16. First portion 20 has a first passageway 22 therethrough that is in fluid connection with tubing 16. Passageway 22 has a first valve 24 therein that is biased in a normally closed position to close first passageway 22 with first valve 24 being operative to an open position as shown in FIG. 2 and indicated by the flow arrows. Disconnect device 18 has a second portion 30 that has a second passageway 32 therethrough with a second valve 34 therein biased in a normally closed position to close second passageway 32 as shown in FIG. 2a. Second valve 34 is also operative to an open position as shown in FIG. 2 and indicated by flow arrows. Second portion 30 is releasably attached at a joint 36 onto first portion 20 to connect the first and second passageways, to overcome the bias of first valve 24 and second valve 34, to operate the valves to their open positions and to allow a fluid flow through the disconnect device. Referring to FIG. 2a, second portion 30 is detachable from first portion 20 at joint 36 by application of a preselected force less than a force required to physically disrupt a medical access device attached to the tubing set. Upon the detachment, as shown in FIG. 2a, first valve 24 and second valve 34 thereby are operative to their normally closed positions.

As seen in FIG. 1, the preferred tubing set also includes a distal tubing portion 38 that is in a fluid connection to second portion 30 with a distal adapter 40 in a fluid connection to distal tubing portion 38 to attach the tubing set in a fluid connection to a medical access device, e.g., a catheter 42 held down by a tape 43 on a skin surface 44.

Valves 24 and 34 are preferably substantially identical. For the purpose of this description, the valves are described and numbered as identical. Each valve has a movable pusher plate 50 with at least one, preferably two channels 52, 53 and resilient elastomeric duckbills 54 with at least one, preferably two closure members 56, 57. Each closure member has elongate flanges 58, 59 slidably positioned within the channels. Each plate 50 is biased, preferably by coil springs 60, so that valves are in the normally closed position as shown in FIG. 2a, where the portions are disconnected. When the disconnect device is connected to allow fluid flow, as shown in FIG. 2, a male member 62 is releasably fit within a female receptacle 63. Each plate 50 has at least one, preferably two, extensions 64 to contact the opposing portion when the disconnect device of the invention is connected. The contact of extensions 64 with the opposing portion overcomes the bias of springs 60, moves plates 50 to actuate valves 24 and 34 to the open position, as shown in FIG. 2, by a slidable movement of flanges 58, 59 in channels 52, 53 as the plate moves. Preferably, male member 62 includes an "O" ring 66 to form a substantially fluid tight seal in receptacle 63. Other forms of seals including gaskets and the like would be satisfactory and are considered within the scope of the invention.

Turning now to FIGS. 3–6a, alternative embodiments of the disconnect device of the present invention are illustrated. In these embodiments, there are some substantially similar components. Some of these components perform substantially similar functions. Accordingly, substantially similar components performing substantially similar functions are numbered identically to those components of the embodiment of FIGS. 1–3a except that the reference characters include hundreds digits to identify those components in FIGS. 4–6a.

In FIGS. 3 and 3a, a disconnect device 118 of the present invention has a first portion 120 with a passage 122 closed by a septum 124, functioning as a valve, that preferably has a pre-cut slit 125 to facilitate penetration by a piercing member. This portion of the disconnect device 118 also has an adapter 119 sized to fit first portion 120. In the case where portion 120 has external threads 121, as is the case for some commercially available septum fittings, adapter 119 preferably has conjugate internal threads 123 to retain the adapter on the first portion. Adapter 119 has a passageway 127 therethrough that exposes septum 124. In this embodiment, second portion 130 has a piercing member 129 with a bore 132 therethrough and a resilient member 133 positioned to normally occlude bore 132 to function as a valve 134. As shown in FIG. 3, valve 134 is operative to an open position by placement of second portion 130 into adapter 119 so that resilient member 133 contacts septum 124. Resilient member 133 has a slit 135 that allows piercing member 129 to protrude and penetrate septum 124 at slit 125 allowing a fluid flow as shown the flow arrows in FIG. 3. Preferably, adapter 119 has a collar 139 that mates with a shoulder 137 to releasably retain the second portion in the adapter. The separation force required for detaching the second portion from the adapter may be varied for particular applications by providing adapter 119 with several variations in collar 139 to provide more or less retentive contact with shoulder 137. The degree of retention may be indicated by a numbering or color code scheme.

Preferably resilient member 133 is biased to normally occlude bore 132 by a coil spring 160 around piercing member 129. When second portion 130 is detached from adapter 119 as is shown in FIG. 3a, resilient member 133 is moved to occlude bore 132 by spring 160 and septum 124 closes to occlude passage 122. Disconnect device 118 may be re-attached after wiping the resilient member and septum and replacing the second portion in the adapter.

Figure 4:
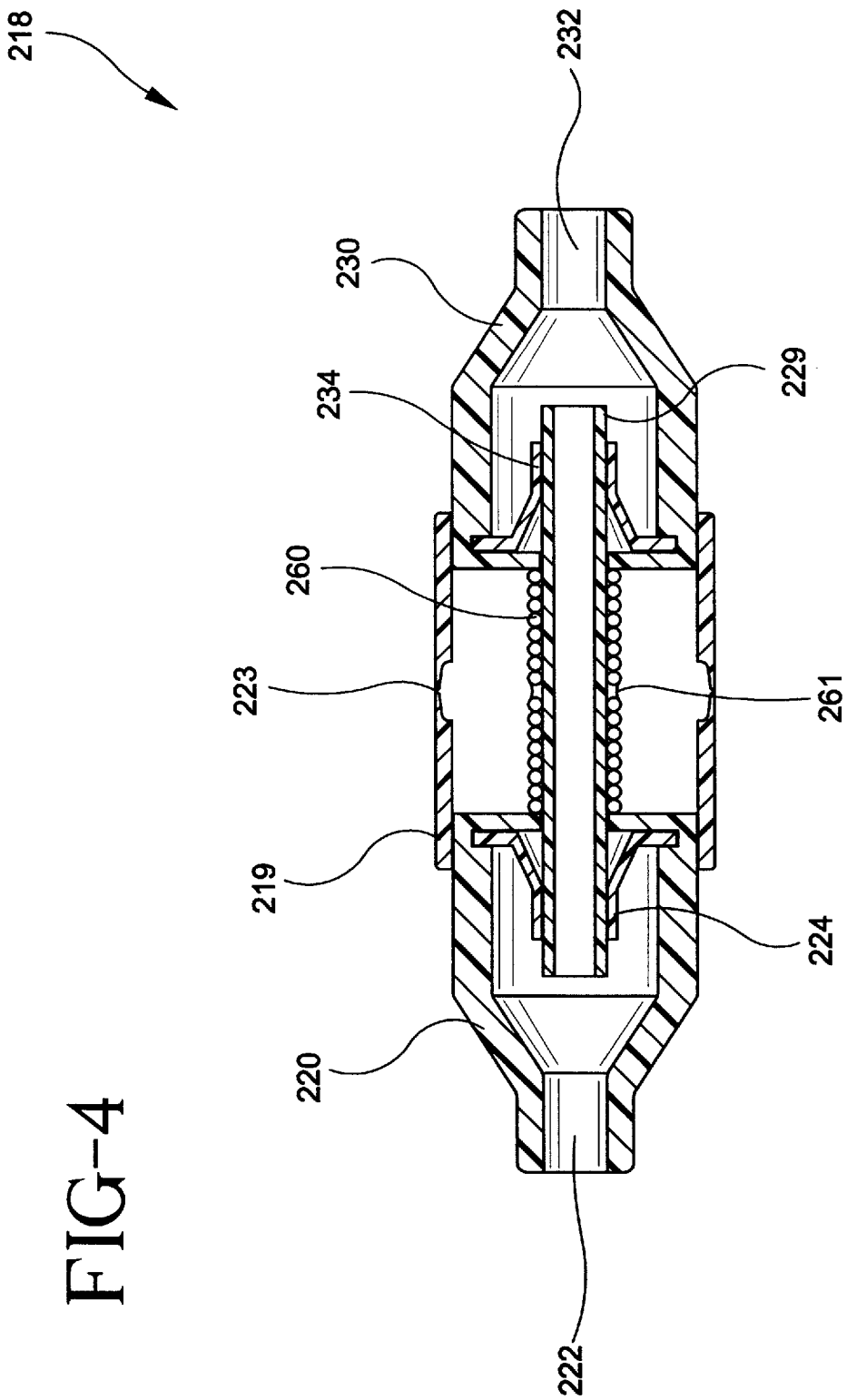
FIG. 4 is a schematic cross-sectional view, analogous to FIG. 2, of another embodiment of the disconnect device of the present invention.

For applications where re-attachment is not desired, the scope of the invention includes a frangible disconnect device as shown in FIGS. 4 and 4a. In FIGS. 4 and 4a, a disconnect device 218 of the present invention includes a first portion 220 with a first passageway 222 that has a first resilient duckbill valve 224 positioned and biased to a normally closed position to close passageway 222. Disconnect device 218 includes a second portion 230 with a second resilient duckbill valve 234 positioned and biased to a normally closed position to close passageway 232. Disconnect device 218 further includes a tube 229 releasably position within portions 220 and 230 to hold resilient duckbill valves 224 and 234 in the open positions and allow a fluid flow as indicated by the flow arrows in FIG. 4.

Disconnect device 218 also includes a frangible member 219 to releasably retain portions 220 and 230 in the connected position shown in FIG. 4. Frangible member 219 may be formed from a polymeric resin such as polyethylene and the like, and have at least one area 223 of reduced thickness to facilitate breakage of the attachment at area 223 with separation of the first portion and second portions as indicated in FIG. 4a. Frangible member 219 is fixedly attached to retain the first and second portions in fluid communication until broken by a preselected force. Suitable attachments for the frangible member to portions 220 and 230 include, but are not limited to, ultrasonic bonding, heat bonding, solvent bonding, adhesive bonding and the like. Ultrasonic bonding is preferred. Preferably, tube 229 has a coil spring 260 attached at a point 261 by a spot weld, crimping or the like, around its outer surface that is compressed between the duckbill valves when the portions are connected, as in FIG. 4. Spring 260 provides a bias to ensure withdrawal of tube 229 from each of the duckbill valves when frangible member 219 is broken by a separation force as shown in FIG. 4a.

The amount of force required to separate the portions may be varied by providing frangible member 219 with several thicknesses at area 223. A color code or numbering scheme corresponding to the several thickness is useful to allow a practitioner to select a disconnect device with the desired separation force. In this embodiment, disconnect device 218 is not re-connectable after detachment. Other forms of frangible members such as paper, films, fibers and the like, as well as integrally forming the frangible member with one or both of the portions of the disconnect may be envisioned, and are considered to be within the scope of the invention.

For some applications, the disconnect device needs only to be valved to one side. For these applications, the embodiments illustrated in FIGS. 5–7a, the disconnect devices are simpler to manufacture than the embodiments illustrated in FIGS. 1–4a. In most cases, the disconnect device is placed in the fluid delivery system so that the valved portion is on the patient side of the fluid delivery system. Thus, when the disconnect device is detached, the valve is closed and the patient is substantially protected from blood loss.

Figure 5A:
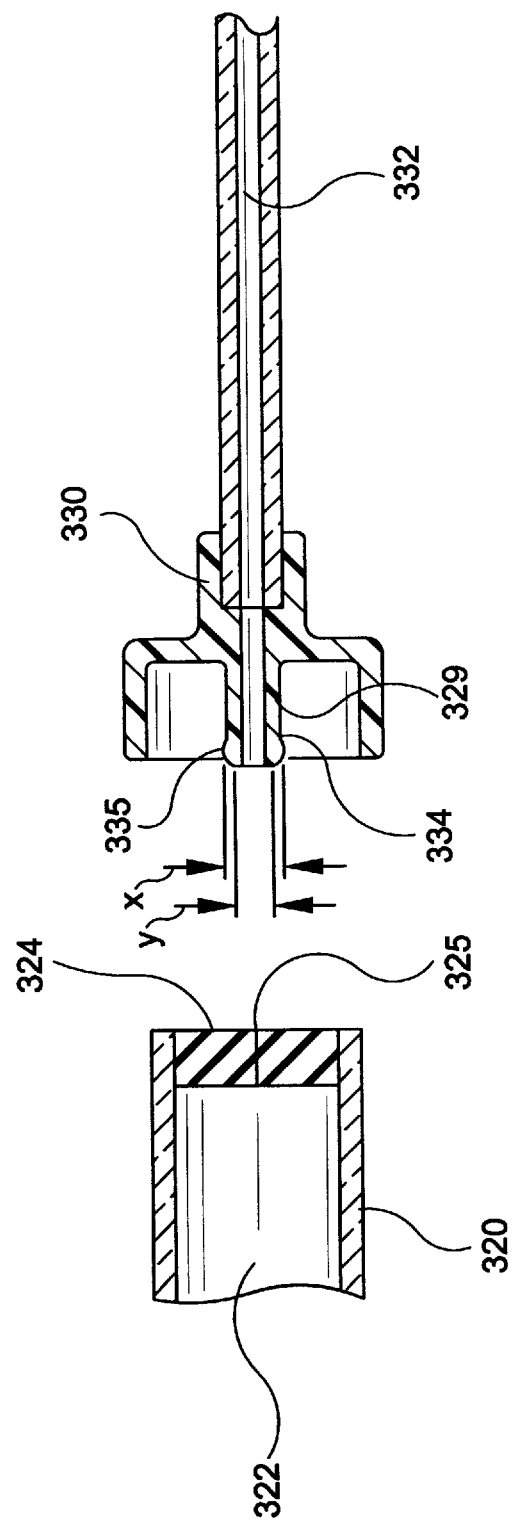
FIG. 5a is a schematic cross-sectional view, analogous to FIG. 2a, of the disconnect device of FIG. 5, as disconnected.

As shown in FIGS. 5 and 5a, a disconnect device 318 has a first portion 320 with a resilient pierceable septum 324. Preferably septum 324 has a slit 325 to facilitate penetration of the septum. Disconnect device 318 also has a second portion 330 sized to mate with first portion 320. Second portion 330 has a piercing member 329 for penetrating the septum. Piercing member 329 is a hollow tube that has an enlargement 335 at tip portion 334, illustrated as a knob, with a larger outside diameter "x" than the outside diameter "y" of the hollow tube to releasably retain the piercing member behind the septum after the penetration. The diameter of knob 334 and the resiliency of the septum may be adjusted to provide a required preselected force for removal of the knob back through the septum and separate the second portion from the first portion. Piercing member 329 has a passageway 332 therethrough to allow fluid flow through the device. Piercing member 329 is withdrawn from septum 324 when second portion 330 is detached from first portion 320 as shown in FIG. 5a. When the portions are detached, septum 324 closes at slit 325 to substantially prevent flow through the first portion. In use, the first portion generally would be placed in the fluid delivery set so that any blood flow from the patient would be substantially occluded if the disconnect device were detached.

Figure 6:
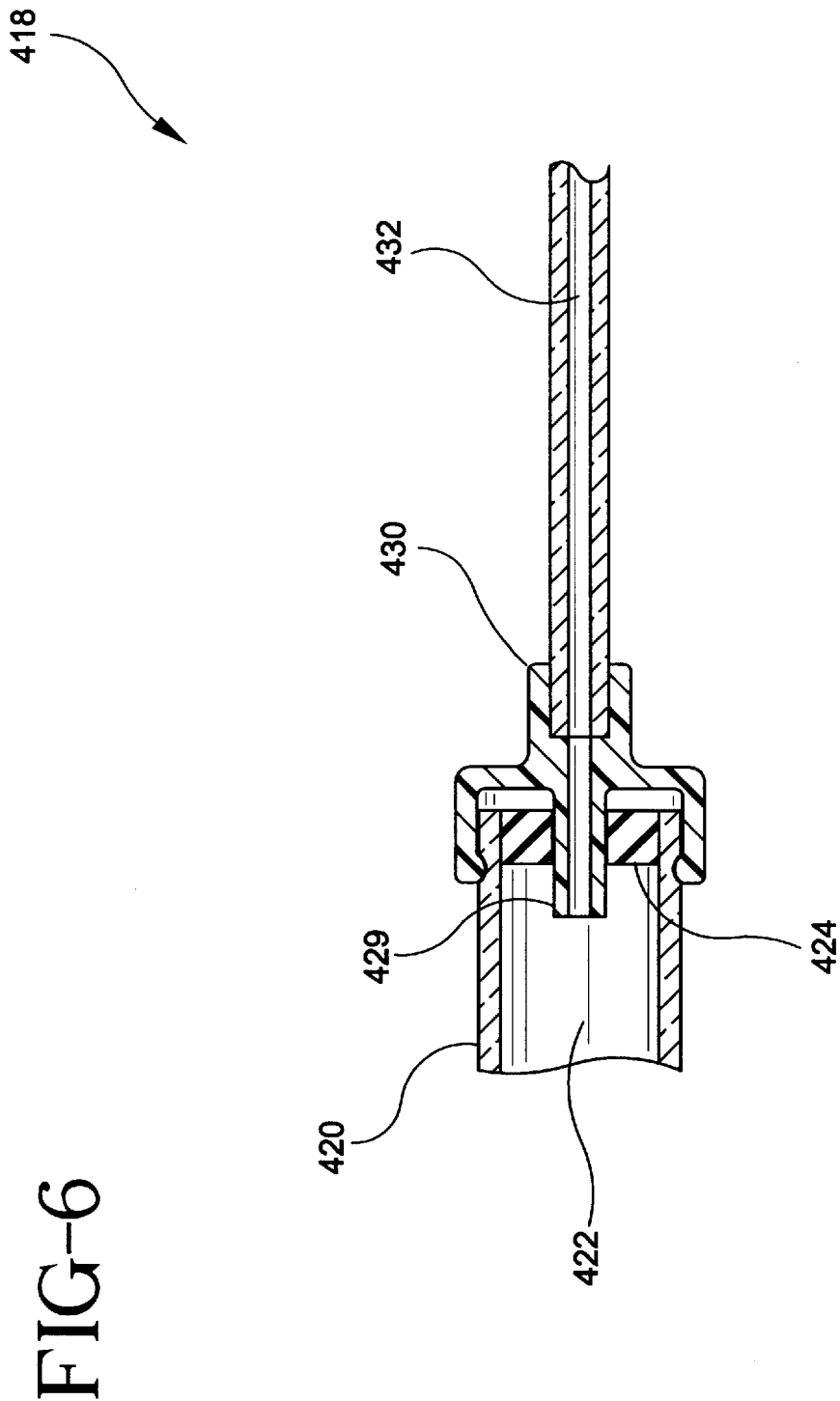
FIG. 6 is a schematic cross-sectional view, analogous to FIG. 2, of a further embodiment of the present invention.
Figure 6A:
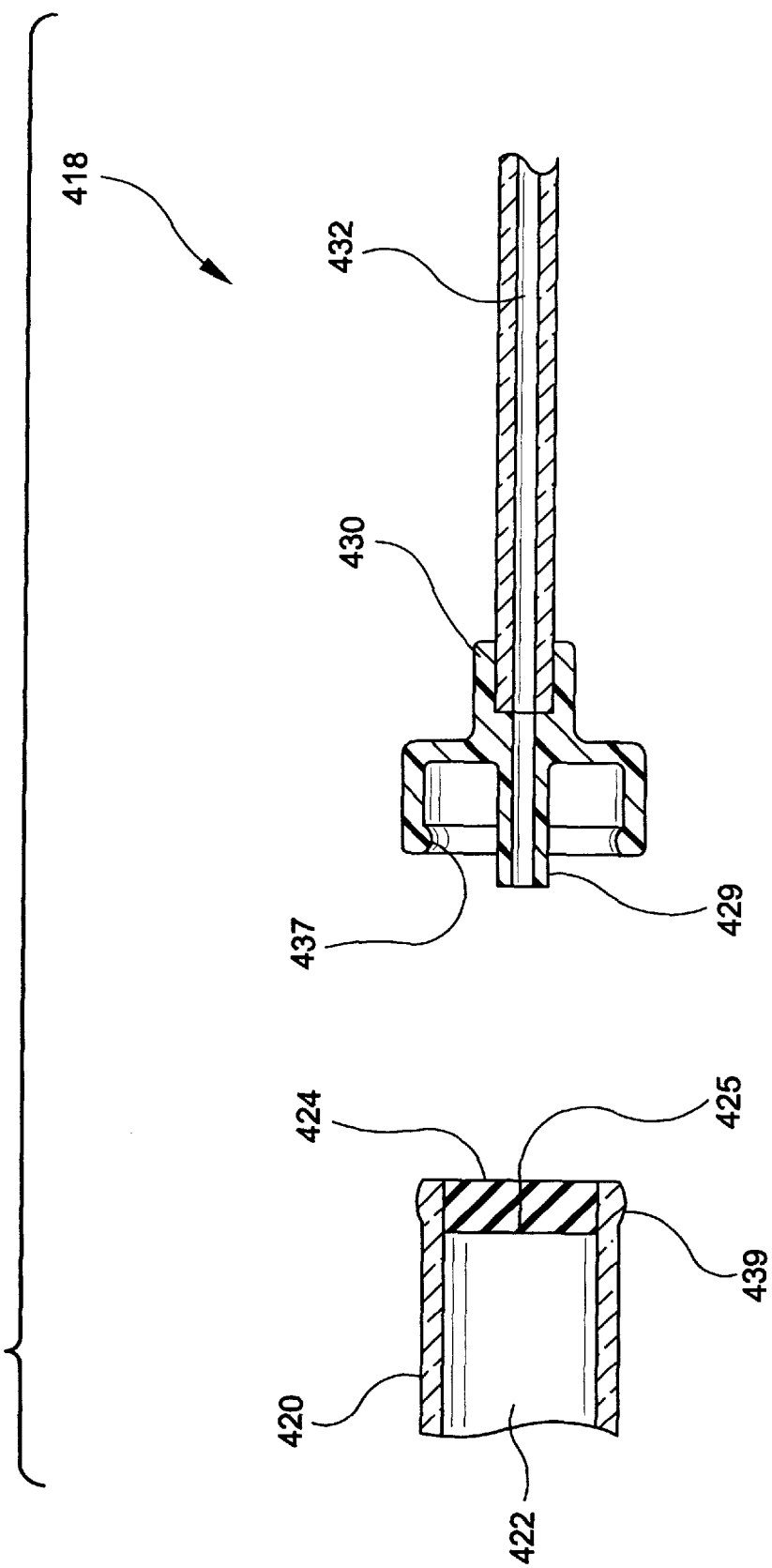
FIG. 6a is a schematic cross-sectional view, analogous to FIG. 2a, of the disconnect device of FIG. 6, as disconnected.

As shown in FIGS. 6 and 6a, another disconnect device 418 of the invention is shown. Disconnect device 418 includes a first portion 420 with resilient pierceable septum 424 that functions as a valve and preferably has a slit 425 to facilitate piercing of the septum. Disconnect device 418 has a second portion 430 sized to mate with portion 420 and includes a piercing member 429. When the first and second portions are mated as shown in FIG. 6, piercing member 429 penetrates septum 424 and allows fluid flow through bore 432 as shown by the flow arrows in FIG. 6. The first and second portions are releasably retained in the mated position by a collar 437 on second portion 430 sized to fit over a shoulder 439 on first portion 420. When the portions are disconnected as shown in FIG. 6a, the piercing member is withdrawn from the septum and fluid flow through the first portion is substantially occluded. The force required to detach the second portion from the first portion may be pre-selected by adjustments to the size of the collar and the shoulder. Other forms of releasably retaining the second portion mated with the first portion such as a snap-fit, and the like are equally satisfactory and are considered within the scope of the invention.

Figure 7:
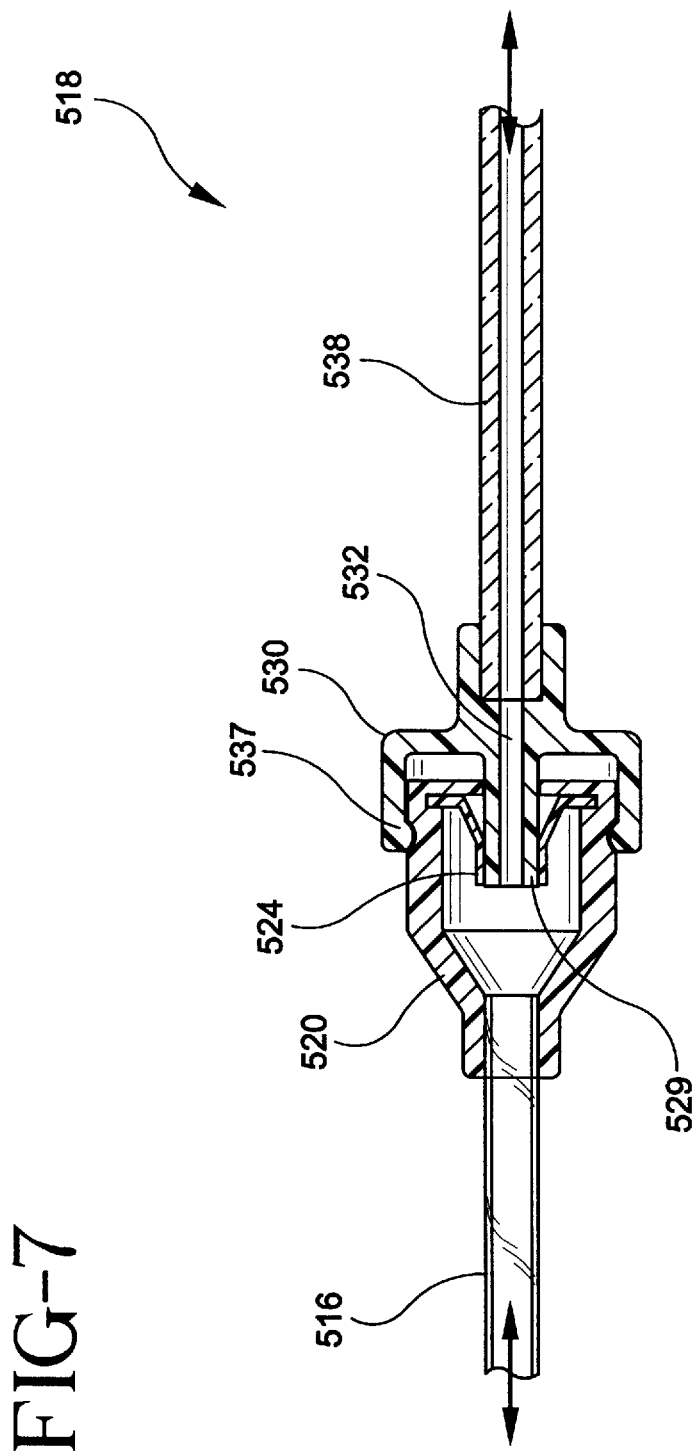
FIG. 7 is a schematic cross-sectional view, analogous to FIG. 2, of a further embodiment of the present invention.

As shown in FIGS. 7 and 7a, a further disconnect device 518 is shown. Disconnect device 518 includes a first portion 520 with valve 524. Disconnect device 518 has a second portion 530 sized to mate with portion 520 and includes a tube 529. When the first and second portions are mated as shown in FIG. 7, tube 529 opens valve 524 and allows fluid flow through bore 532 as shown by the flow arrows in FIG. 7. The first and second portions are releasably retained in the mated position by a collar 537 on second portion 530 sized to fit over a shoulder 539 on first portion 520. When the portions are disconnected as shown in FIG. 7a, the tube is withdrawn from the valve and fluid flow through the first portion is substantially occluded. The force required to detach the second portion from the first portion may be pre-selected by adjustments to the size of the collar and the shoulder. Other forms of releasably retaining the second portion mated with the first portion such as a snap-fit, and the like are equally satisfactory and are considered within the scope of the invention.

Figure 8:
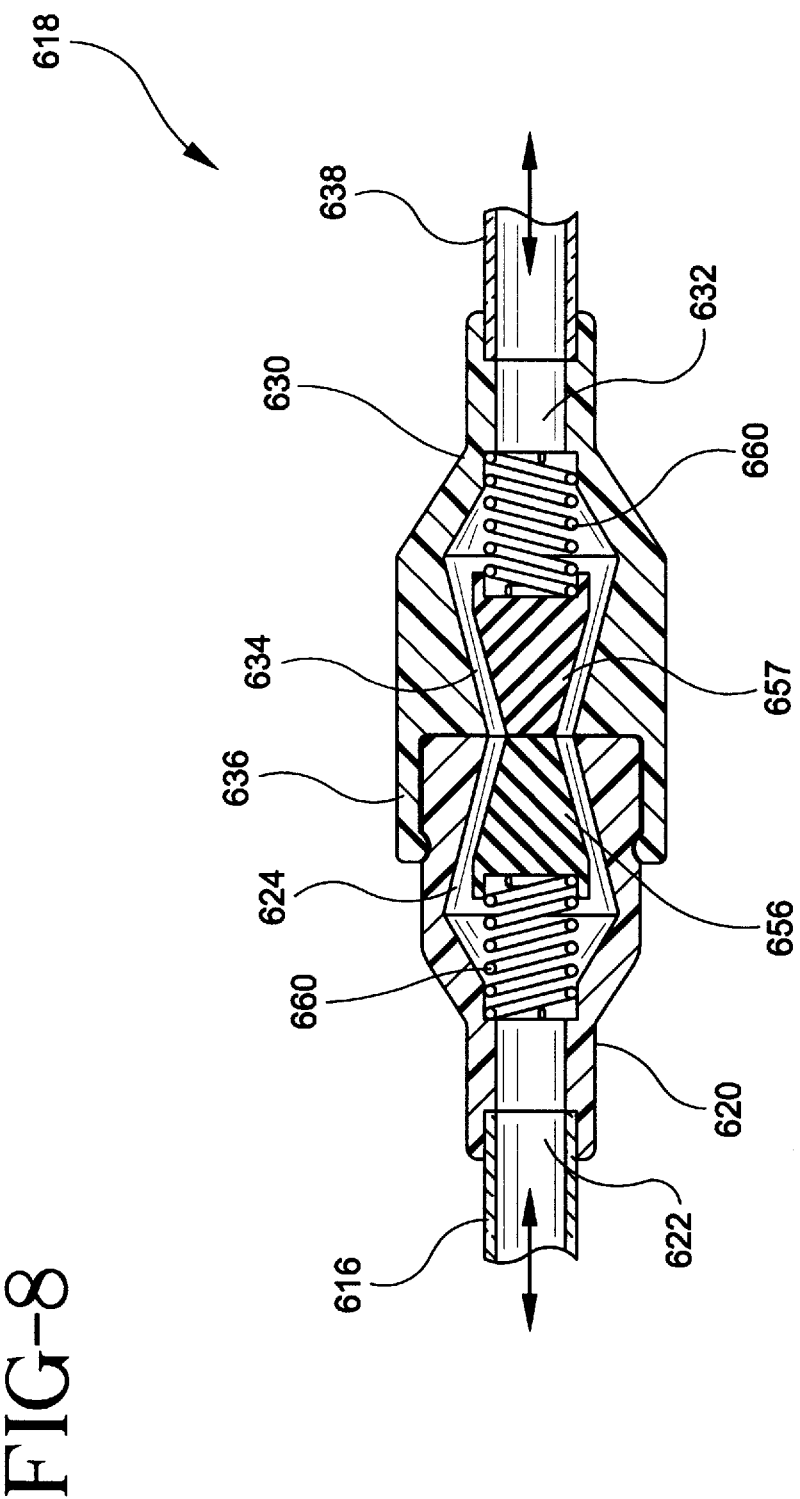
FIG. 8 is a schematic cross-sectional view, analogous to FIG. 2 of a further embodiment of the present invention.

Referring to FIGS. 8 and 8*a*, another disconnect device 618 is shown. Disconnect device 618 is similar in function to the preferred disconnect device of FIGS. 1–2*a*. Device 618 has first portion 620 with first valve 624 having a movable valve portion 656 and second portion 630 with second valve 634 having a movable valve portion 657. Valves 624 and 634 are biased by springs 660 to a normally closed position to occlude fluid flow. When disconnect device is in the connected position as illustrated in FIG. 8, valves 624 and 634 are operated to an open position by contact between valve portions 656 and 657 to overcome the bias provided by springs 660. When the portions are detached from each other, as illustrated in FIG. 8*a*, bias springs 660 move valve portions 656 and 657 to their normally closed positions and substantially occlude fluid flow.

Resilient elastomeric materials such as natural rubber, silicone rubber, polychloroprene, polyurethane and the like with a Shore A durometer between about 30 to about 80 are suitable for forming the septum, duckbill valves and other resilient members. Preferably, a silicone elastomer with a Shore A durometer about 50 is used. Body materials may be formed from polymeric materials such as polyethylene, polypropylene, polycarbonate, polyester, polyamide and the like. Polycarbonate is preferred for the mechanically retained embodiments as shown in FIGS. 1–3 and 5–6*a* with polyethylene being preferred for the frangible embodiments. Coil springs used to provide bias in the several embodiments of the disconnect device of the present invention preferably are formed from substantially inert materials such as stainless steel and the like. Type 304 stainless steel is often selected for medical device applications and is suitable for use in the present invention.

When the disconnect device of present invention is used with common tubing sets, that have polyvinylchloride (PVC) tubing, the disconnect device may be fitted with luer type adapters and the like to allow the invention to be installed either proximally at the fluid source or distally at the site of the catheter or other fluid delivery device directly at the patient. The PVC tubing commonly used in medical tubing sets has a break force about twenty kg. Many of the small diameter silastic elastomer tubes used in catheters for long term implantation have a break force less than one kg. Separation of a catheter hub from a patient's arm that is taped down following a commonly used tape technique requires about three to four kg. Catheter attachments also often utilize sutures to fix the catheter to the patient. Once a catheter is released from the attachment point, little additional force is required to withdraw it from the body if the force is applied in a linear manner. In the case of application of an accidental force, the attachment may be disrupted with the catheter subsequently being broken off as the force direction changes. The ability to provide disconnect devices of the present invention with preselected detachment forces between about 0.25 kg to about 8 kg enable a practitioner to select a disconnect to protect different kinds of catheters in different situations, e.g., a low separation force for a neonate with a very small catheter or a higher separation force for an ambulatory and active patient.

Infusion therapy, intravenous catheters, feeding tubes and similar medical access devices are widely used in hospitals and now even on patients in fully ambulatory home care. When infusion therapy is used with a cooperative bed-ridden patient, there is a small probability of disruption of the medical access device. However, with the wide usage of infusion therapy, ambulatory patients, home care patients and uncooperative or confused patients often require an infusion device. When an accidental force is applied to infusion set tubing, the tubing generally does not break, instead it often transfers the force to the medical access device. This may result in possibly pulling the device off or out of the patient, or worse yet, breaking it off, possibly leaving a portion of the device inside the patient. The disconnect device of the invention substantially eliminates these potentially lethal incidents by disconnecting the tubing with an application of force that is less than the force that would potentially physically disrupt the medial access device. The disconnect device of the invention substantially eliminates physical disruption of the medical access device and increases the margin of safety to patients, particularly non-hospitalized fully ambulatory patients.

What is claimed is:

1. A disconnect device, comprising:

a first housing defining an interior;

a first element valve disposed in the first housing;

a first plate disposed in the first housing slidingly engaging the first valve element for axial movement with respect to the first valve element;

a first spring disposed in the first housing abutting the first plate to bias the first plate against the first valve element and thereby close the first valve element;

a first connector operably connected to the first housing;

a second housing defining an interior;

a second valve element disposed in the second housing;

a second plate disposed in the second housing slidingly engaging the second valve element for axial movement with respect to the second valve element;

a second spring disposed in the second housing abutting the first plate to bias the second plate against the second valve element and thereby close the second valve element;

a second connector operably connected to the second housing whereby when the first connector is connected to the second connector, the first plate is axially moved along the first valve element against the bias of the first spring to thereby open the first valve element and the second plate is axially moved along the second valve element against the bias of the second spring to thereby open the second valve element.

2. The disconnect device of claim 1 wherein the first and second valve elements are each duckbills with at least one closure member.

3. The disconnect device of claim 2 wherein the first plate includes a first axially extending extension and the second plate includes a second axially extending extension wherein the first extension engages the second extension when the first connector is connected to the second connector.

4. The disconnect device of claim 3 wherein the first connector is a male member and the second connector is a female member.

5. The disconnect device of claim 4 further including a fluid tight seal between the male member and the female member when the male member is connected to the female member.

6. A disconnect device, comprising:

a first housing defining an interior;

a first valve element disposed in the first housing;

a plate disposed in the first housing slidingly engaging the first valve element for axial movement with respect to the first valve element;

a spring disposed in the first housing abutting the plate to bias the plate against the first valve element and thereby close the first valve element;

a first connector operably connected to the first housing;

a second housing defining an interior;

a second valve element disposed in the second housing; and a second connector operably connected to the second housing whereby when the first connector is connected to the second connector, the first plate is axially moved along the first valve element against the bias of the spring to thereby open the first valve element and the second valve is opened.

7. The disconnect device of claim 6 wherein the first valve element is a duckbill with at least one closure member.

8. The disconnect device of claim 7 further including a fluid tight seal between the first connector and the second connector when the first connector is connected to the second connector.

9. A disconnect device, comprising:

a first housing defining an interior;

a first valve element disposed in the first housing having at least one closure member with a flange formed therein;

a first plate having a channel formed therein disposed in the first housing and about the first valve element with the flange slidingly engaging the channel for axial movement with respect to the first valve element;

a first spring disposed in the first housing abutting the first plate to bias the first plate against the first valve element and thereby close the first valve element;

a first connector operably connected to the first housing;

a second housing defining an interior;

a second valve element disposed in the second housing; and a second connector operably connected to the second housing whereby when the first connector is connected to the second connector, the first plate is axially moved along the first valve element against the bias of the spring and the channel moves along the flange to thereby open the first valve element.

10. The disconnect device of claim 9 wherein the second valve element is resilient and elastomeric and has a second closure member with a second flange formed therein.

11. The disconnect device of claim 10 further comprising a second plate having a second channel formed therein disposed in the second housing and about the second valve element with the second flange slidingly engaging the second channel for axial movement with respect to the first valve element to open and close the second valve element.

12. The disconnect device of claim 11 further including a second spring disposed in the second housing abutting the second plate to bias the second plate against the second valve element and thereby close the second valve element.

* * * * *